United States Patent [19]

Sugimoto et al.

[11] 4,048,158
[45] Sept. 13, 1977

[54] D-α-ISOBUTYLSULFOBENZYLPENICILLIN HEMI-SOLVATE CRYSTALS

[75] Inventors: Keiichi Sugimoto, Kawanishi; Koji Nishijima, Ibaraki; Tadashi Hanaoka, Suita; Hiroshi Akimoto, Nishinomiya; Nobuharu Kakeya, Kawanishi, all of Japan

[73] Assignee: Takeda Chemical Industries, Ltd., Osaka, Japan

[21] Appl. No.: 645,913

[22] Filed: Dec. 31, 1975

[30] Foreign Application Priority Data

Jan. 20, 1975 Japan .................................. 50-8998

[51] Int. Cl.$^2$ ............................................ C07D 499/62
[52] U.S. Cl. ................................. 260/239.1; 424/271
[58] Field of Search ................................... 260/239.1

[56] References Cited

U.S. PATENT DOCUMENTS 3,674,776   7/1972   Long et al. .................... 260/239.1

FOREIGN PATENT DOCUMENTS 807,482   12/1973   Belgium ............................. 260/239.1
1,003,894   3/1952   France .............................. 260/239.1

OTHER PUBLICATIONS

Nayler et al., Nature, vol. 195, pp. 1264-1267 (1962).
Flynn, "Cephalosporins and Penicillins" p. 519.
Trenner et al., J.A.C.S. vol. 70, pp. 2897-2900 (1948).

*Primary Examiner* — Gerald A. Schwartz
*Attorney, Agent, or Firm* — Wenderoth, Lind & Ponack

[57] ABSTRACT

Novel d-α-isobutylsulfobenzylpenicillin hemi-solvate crystals of the formula:

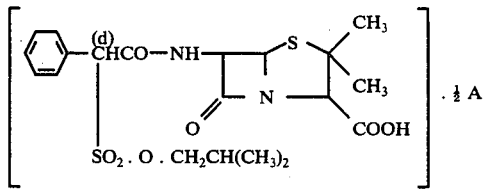

(wherein A is a solvent selected from the class consisting of alcohols, ketones, ethers and esters) have excellent antibacterial activities and improved stability in terms of shelf-life.

7 Claims, No Drawings d-α-ISOBUTYLSULFOBENZYLPENICILLIN HEMI-SOLVATE CRYSTALS

The present invention relates to novel d-α-isobutylsulfobenzylpenicillin hemi-solvate crystals. More concretely, the present invention relates to d-α-isobutylsulfobenzylpenicillin hemi-solvate crystals represented by the formula (I):

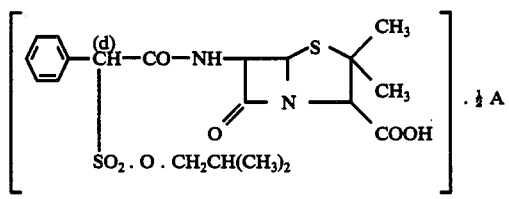

(wherein A is a solvent selected from the class consisting of alcohols, ketones, ethers and esters).

The present inventors previously succeeded in the development of α-alkylsulfobenzylpenicillins which have excellent thereapeutic effects upon the infectious diseases caused by gram-positive and gram-negative bacteria, are particularly eminently inhibitory against strains of the genus Pseudomonas, stable against penicillinase and, moreover, lend themselves to administration by the oral route (See the specification of Japanese patent application No. 79606/1973 or Belgian Pat. No. 807,482). However, these α-alkylsulfobenzylpenicillins generally were found to be more or less unstable in terms of the so-called shelf-life, and nonwithstanding the fact that α-isobutylsulfobenzylpenicillin, among them, is one of the relatively stable compounds, its shelf-life remained yet to be improved.

By the same token, α-isobutylsulfobenzylpenicillin as it is produced by the production process described in the specification of the above-mentioned Japanese patent application No. 79606/1973 or Belgian Pat. No. 807,482 is secured in the form of free acid or a nontoxic salt. In view of the fact that medicaments in general were preferably made available in the form of crystals which had comparatively long shelf-lives, many attempts were made to obtain not only free α-isobutylsulfobenzylpencillin but also various nontoxic salts thereof (alkali metal salts, alkaline earth metal salts, nontoxic amine salts, etc.) in crystalline condition. In most of these attempts merely amorphous product was obtained, and in a very limited number of cases crytalline product admixed with a substantial amount of amorphous product was obtained, separation of the crystalline product from the amorphous product being highly complicated and hardly tractable. Thus none of the attempts has so far proved to be successful.

These problems were thoroughly examined and studied by the present invention. As a result, they discovered:

1. that if a certain organic solvent is present in the crystallization system of d-α-isobutylsulfobenzylpenicillin, the latter crystallizes in the form of the corresponding organic solvate;

2. that when said organic solvate crystallizes out of a system comprising a mixture of d-α-isobutylsulfobenzylpencillin and l-α-isobutylsulfobenzylpencillin, the d-α-isobutylsulfobenzylpenicillin hemi-solvate separates out preferentially; that is to say the operation permits resolution of optical isomers of the penicillin;

3. that the mole ratio of d-α-isobutylsulfobenzylpenicillin to the solvent in the above solvate is 2:1; that is to say, there is obtained a d-α-isobutylsulfobenzylpenicillin hemi-solvate of the above formula (I);

4. that the d-α-isobutylsulfobenzylpenicillin hemi-solvate thus obtained is not amorphous but crystalline;

5. that a trans-solvation, that is to say, a replacement of the solvent of crystallization in the thus obtained d-α-isobutylsulfobenzylpenicillin hemi-solvate crystals with a different solvent of crystallization may be accomplished by recrystallizing these crystals from one of said specific solvents other than the solvent of crystallization in the starting hemi-solvate crystals;

6. that d-α-isobutylsulfobenzylpenicillin hemi-solvate crystals display a considerably longer shelf-life than that of α-isobutylsulfobenzylpencillin itself or of its salts;

7. that, in spectroscopic analysis, d-α-isobutylsulfobenzylpenicillin hemi-solvate crystals are substances clearly distinct from d-α-isobutylsulfobenzylpenicillin and its salts; and 8. that d-α-isobutylsulfobenzylpenicillin hemi-solvate crystals display as high an antibiotic activity against gram-positive and gram-negative bacteria, are as stable against penicillinase and, in particular, display as much prominent therapeutic effects upon Pseudomonas infections, as α-isobutylsulfobenzylpenicillin, the d-form thereof, and their notoxic salts.

Following these and other unexpected findings, the present inventors made further studies and have finally developed this invention.

The objective compound of this invention is provided by a method which comprises crystallizing d-α-isobutylsulfobenzylpenicillin hemi-solvate crystals out of a liquid phase comprising d-α-isobutylsulfobenzylpenicillin, or as is more frequently the case, a mixture of d- and l-α-isobutylsulfobenzylpenicillins, and a solvent selected from the class consisting of alcohols, ketones, ethers and esters and, if desired, recrystallizing transsolvated d-α-isobutylsulfobenzylpenicillin hemi-solvate crystals out of a liquid phase prepared from the first-mentioned d-α-isobutylsulfobenzylpenicillin hemi-solvate crystals and a solvent selected from the class consisting of alcohols, ketones, ethers and esters excepting the solvent used for the above crystallization.

It should be understood that, in the practice of the method of this invention, mixtures of optional proportions of d- and l-isomers, including the d,l-racemic mixture, may also be employed as the starting material.

While d- or d,l-α-isobutylsulfobenzylpenicillin may be produced by the method described in the specification of Japanese patent application No. 79606/1973 and the specification of Belgian Pat. No. 807,482, these compounds may be used in the practice of this invention as isolated compounds or, alternatively, solutions containing such compounds (for example, a reaction mixture after the acylation reaction for the production of d,l-α-isobutylsulfobenzylpenicillin) may be employed.

Further as to the preparation of the starting material, it is to be noted that d-α-isobutylsulfobenzylpenicillin is less soluble in a solvent than l-α-isobutylsulfobenzylpenicillin. Thus by suspending d,l-α-isobutylsulfobenzylpenicillin in a solvent and recovering the insoluble fraction, a dextrorotatory-rich mixture of d-α-isobutylsulfobenzylpenicillin and l-α-isobutylsulfobenzylpenicillin can be obtained. In this manner, d-α-isobutylsulfobenzylpenicillin in high optical purity can be obtained by completely dissolving l-α-isobutylsulfobenzylpenicillin out and separating the solution containing l-α-isobutylsulfobenzylpenicillin from the solid d-α-isobutylsulfobenzylpenicillin. The specific rotations of these optical isomers are as follows.

d-α-Isobutylsulfobenzylpenicillin
$[\alpha]_D^{20} = +149°$(CHCl$_3$, c=1.0)
l-α-Isobutylsulfobenzylpenicillin
$[\alpha]_D^{20} = +115°$(CHCl$_3$, c=1.0)

As the aforementioned solvent for the above preparation, any of the undermentioned solvents may be employed. Above all else, however, diisopropyl ether, isopropyl alcohol and so on are particularly beneficial in view of solubility.

As the alcohols which are employed as the solvent represented by A in the formula (I), there may be mentioned methyl alcohol, ethyl alcohol, n-propyl alcohol, isopropyl alcohol, n-butyl alcohol, etc. The ketones are exemplified by acetone, methyl ethyl ketone, methyl isobutyl ketone and so on. The ethers include diethyl ether, diisopropyl ether, dioxane and so on. As said esters, there may be mentioned ethyl acetate, methyl acetate and so on. Particularly advantaqeous are alcohols of 1 to 4 carbon atoms, ethers of 4 to 6 carbon atoms, ketones of 3 to 6 carbon atoms and esters of 3 to 6 carbon atoms.

This invention is generally carried into practice by causing d-α-isobutylsulfobenzylpenicillin hemi-solvate to crystallize out of a solution containing d-α-isobutylsulfobenzylpenicillin, or d- and l-α-isobutylsulfobenzylpenicillins, as well as a solvent selected from the class consisting of alchols, ketones, ethers and esters, and recovering the crystalline product thus obtained by means such as filtration.

More specifically, as preferred procedures for crystallization, the following may be mentioned.

1. The procedure which comprises dissolving the starting material in one of the above-specified organic solvents and causing the desired product (i.e. d-α-isobutylsulfobenzylpenicillin hemi-solvate crystals) to crystallize by taking advantage of their temperature-specific difference is solubility. The solubility capacity of the solvent system decreases as the temperature of the solution is lowered. Thus, when the temperature of the solution is so lowered that the solvent system is not able to dissolve all of the starting penicillin compound, d-α-isobutylsulfobenzylpenicillin hemi-solvate crystals begin to be precipitated.

2. The procedure which comprises dissolving the starting material in one of the above-specified solvents and, then, adding a solvent, in which the desired product is hardly soluble, to the solution. The solubility capacity of the solvent system is decreased by the addition of a solvent in which the desired product is hardly soluble. Thus, when the solubility capacity of the solvent system is so decreased that the solvent system is not able to dissolve all of the starting penicillin compound, d-α-isobutylsulfobenzylpenicillin hemi-solvate crystals begin to be precipitated.

3. The procedure which comprises dissolving the starting material in one of the above-specified solvents and, then, decreasing the amount of solvent by distilling off the solvent to thereby concentrate the solution.

The solubility capacity of the solvent system is decreased by the decrease of the amount of the solvent by distillation. Thus, when the amount of the solvent is so decreased that the solvent system is not able to dissolve all of the starting penicillin compound, d-α-isobutylsulfobenzylpenicillin hemi-solvate crystals begin to be precipitated.

As to the precipitation in case when a mixture of d-α-isobutylsulfobenzylpenicillin and l-α-isobutylsulfobenzylpenicillin is used as the starting material, it is to be understood that firstly d-α-isobutylsulfobenzylpenicillin hemi-solvate crystals are solely precipitated, and then d-α-isobutylsulfobenzylpenicillin hemi-solvate crystals mixed with amorphous l-α-isobutylsulfobenzylpenicillin begin to be precipitated. After completion of the precipitation of the mixture, there remains l-α-isobutylsulfobenzylpenicillin in the solution. The mixture is undesired, because it is very complicated and difficult to separate the crystalline product from the amorphous product. Therefore, in the present invention d-α-isobutylsulfobenzylpenicillin hemi-solvate crystals precipitated at the first stage, i.e. before the commencement of the precipitation of the mixture, are collected for example by filtration. The commencement of precipitation of the mixture can be determined by observing the change of the specific rotation of the precipitated product, because the specific rotation value of the d-α-Isobutylsulfobenzylpenicillin is larger than that of the l-isomer, as mentioned above.

It is to be noted that the above three procedures may be adopted singly or in combination.

The solvent in which the desired product is hardly dissolved and which is to be added to a solution of d-α-isobutylsulfobenzylpenicillin in case of the above procedure (2), is exemplified by water, n-haxane, petroleum ether, benzene and toluene.

When the solvent is distilled off in the above procedure (3), the distillation is carried out with advantage under reduced pressure.

The solvent used for dissolving the starting material, that is to say one of said alcohols, ketones, ethers and esters, may include other solvents.

For example, the solubility of the starting material is rather improved by the presence of dichloromethane, dichloroethane, chloroform, dimethylsulfoxide or dimethylformamide, to mention but a few.

Since penicillins generally tend to decompose at temperatures over about 50° C, the above operation is normally carried out at a temperature between about 10° C below the freezing point and about 50° C, preferably between about 0° C and about 35° C.

After collection of d-α-isobutylsulfobenzylpenicillin hemi-solvate crystals, the crystals are dried according to per se known means to obtain the desired product.

Furthermore, if desired, the solvent of crystallization in thus-obtained d-α-isobutylsulfobenzylpenicillin hemi-solvate crystals may be replaced with a different solvent selected from the said class consisting of alcohols, ketones, ethers and esters.

In this case, the product d-α-isobutylsulfobenzylpenicillin hemi-solvate crystals are used as the starting material and one of the above-described crystallization procedures is carried out. And in this case a desired specified organic solvent other than the solvent of crystallization of starting hemi-solvate crystals is used in lieu of the specified organic solvent used in the preceding crystallization procedure.

In this manner, the desired exchange of solvents of crystallization may be accomplished. For example, in a particularly desirable embodiment of this invention, the solvent of crystallization in the hemi-solvate crystals obtained on optical resolution of d,l-α-isobutylsulfobenzylpenicillin with diisopropyl ether is replaced with ethanol to obtain an end product highly suited for oral adiminstration.

The ratio of the said specified organic solvent (recrystallization solvent) to the solvent of crystallization in starting hemi-solvate crystals is normally a large excess and, although the threshold value cannot be stated in general terms, it is normally sufficient to employ about twice to 20 times on the weight basis.

The resultant product may be recovered and dried in the same manner as already described. The d-α-isobutylsulfobenzylpenicillin.½ mol ethyl alchohol crystals which can thus be produced by the method of this invention may, under some circumstances, assume two or more different crystalline forms or patterns, but all such patterns display excellent shelf-lives, are covered by this invention, and are of value as medicaments.

For example, as to the d-α-isoubtylsulfobenzylpenicillin.½ mol ethyl alcohol crystals which separate from an ethyl alcohol-water system, there have been found two patterns, i.e. the β-crystals which are obtained immediately after the start of crystallization and the α-crystals which are formed after the proportion of water in the crystallization system is increased and the latter is stirred well. It has also been found that, on heating (for example, to 40° C), the β-crystals are transformed into said α-crystals.

The difference between α-crystals and β-crystals has been found in the infrared absorption band at 1760 to 1769 cm$^{-1}$, as mentioned below in Table 1.

The spectrometric characteristics of the d-α-isobutylsulfobenzylpenicillin hemi-solvate crystals produced according to this invention are that, their infrared absorption spectrum (KBr disc) give sharp absorption bands characteristic of crystal form at 1550 cm$^{-1}$, 1670 cm$^{-1}$ and 1790 cm$^{-1}$ regions and, in powder X-ray diffraction pattern, they show sharp diffraction intensities.

The product compounds of this invention may each be administered alone or together with excipients known per se for example starch, in such dosage forms as powders, granules, tablets, capsules, suppositories, injection and so on. Such dosage forms are prepared according to the conventional procedures. In case of the oral administration, the unit dosage for an adult human is usually in the range from 0.1 to 1 gram of d-α-isobutylsulfobenzylpenicillin hemi-solvate crystals. The unit dosage is administered every one to several hours in the case of Pseudomonas infections, for instance.

REFERENCE EXAMPLE 1

1. In 500 ml of diisopropyl ether including 10% of dichloromethane was suspended 10 g of d,l-α-isobutylsulfobenzylpenicillin. The suspension was stirred at 20° C for 30 minutes, after which it was suction-filtered. The solid was rinsed with 50 ml of diisopropyl ether and, at room temperature, dried under reduced pressure for 8 hours. The procedure provided 3.2 g of d-α-isobutylsulfobenzylpenicillin.

Optical purity 100% ($[\alpha]_D^{20}$ = +149°, CHCl$_3$, c=1.0), on the basis of non-solvated penicillin.

2. In 1 l of diisopropyl ether was suspended 10 g of d,l-α-isobutylsulfobenzylpenicillin and the suspension was stirred at 20° C for 30 minutes.

It was then suction-filtered and the solid matter was rinsed with 50 ml of diisopropyl ether and, at room temperature, dried under reduced pressure for 8 hours. The procedure provided 4.3 g of d-α-isobutylsulfobenzylpenicillin.

Optical purity 92.5% ($[\alpha]_D^{20}$ = +144°, CHCl$_3$, c=1.0), on the basis of non-solvated penicillin.

EXAMPLE 1

In 200 ml of dichloromethane was dissolved 40 g of d,l-α-isobutylsulfobenzylpenicillin, and following the addition of 200 ml of diisopropyl ether, the solution was concentrated under reduced pressure to 150 ml. The concentrate was stirred at room temperature for 1 hour, whereupon crystals formed. These crystals were recovered by suction-filtration, rinsed with 50 ml of diisopropyl ether and dried at room temperature and under reduced pressure for 8 hours. The procedure provided 13 g of crystals of d-α-isobutylsulfobenzylpenicillin.½ mol diisopropyl ether.

EXAMPLE 2

In 400 ml of isopropyl alcohol was dissolved 20 g of d,l-α-isobutylsulfobenzylpenicillin and, at 20° C, 1000 ml of n-hexane was added dropwise over 60 minutes. After cooling to 10° C, the mixture was stirred for 30 minutes, whereupon crystals formed. These crystals were recovered by suction-filtration, rinsed with 50 ml of n-hexane and dried at room temperature and under reduced pressure for 10 hours. The procedure provided 6 g of crystals of d-α-isobutylsulfobenzylpenicillin.½ mol isopropyl alcohol.

EXAMPLE 3

In 60 ml of acetone was dissolved 5 g of d-α-isobutylsulfobenzylpenicillin and, at 20° C, 40 ml of water was added dropwise over a period of 30 minutes, whereupon crystals formed. After stirring at the same temperature for an additional hour, the crystals were recovered by suction-filtration, rinsed with 25 ml of 60% aqueous acetone and dried at room temperature and under reduced pressure in the presence of anhydrous calcium chloride. The procedure provided 3.6 g of crystals of d-α-isobutylsulfobenzylpenicillin.½ mol acetone.

EXAMPLE 4

To 100 ml of an ethyl acetate solution containing 10 g d-α-isobutylsulfobenzylpenicillin, there was added 1000 ml of n-hexane at 20° C over a period of 60 minutes, whereupon crystals formed. After the dropwise addition, the mixture was further stirred at the same temperature for 60 minutes. The crystals were recovered by suction-filtration, rinsed with 50 ml of n-hexane including 10% of ethyl acetate, and dried at room temperature and under reduced pressure for 8 hours. The procedure provided 8.0 g of crystals of d-α-isobutylsulfobenzylpenicillin .½ mol ethyl acetate.

EXAMPLE 5

In 100 ml of ethyl alcohol was dissolved 10 g of d-α-isobutylsulfobenzylpenicillin and, at 20° C, 100 ml of water was added dropwise over a period of 30 minutes, whereupon crystals formed. The system was cooled to 5° C and, following the addition of 300 ml water, it was stirred at that temperature for 2 hours.

The crystals were recovered by suction-filtration, rinsed with 30 ml of a 20% aqueous solution of ethanol and dried at room temperature and under reduced pressure in the presence of anhydrous calcium chloride for 8 hours. The procedure provided 8.5 g of α-crystals of d-α-isobutylsulfobenzylpenicillin.½ mol ethyl alcohol.

EXAMPLE 6

In 1 l of ethyl alcohol was dissolved 100 g of d-α-isobutylsulfobenzylpenicillin.½ mol diisopropyl ether crystals and, at 15° C, 1 l of water was added dropwise over a period of 60 minutes, whereupon crystals formed. The system was cooled to 5° C and, following the addition of 3 l of water, it was further stirred at that temperature for 2 hours. The crystals were then recovered by suction-filtration, rinsed with 500 ml of a 20% aqueous solution of ethanol and dried at room temperature and under reduced pressure in the presence of anhydrous calcium chloride for 10 hours. The procedure provided 80 g of α-crystals of d-α-isobutylsulfobenzylpenicillin.½ mol ethyl alcohol.

EXAMPLE 7

In 50 ml of ethyl alcohol was dissolved 5 g of d-α-isobutylsulfobenzylpenicillin.½ mol diisopropyl ether crystals and, at 15° C, 50 ml of water was added dropwise over a period of 60 minutes, whereupon crystals formed. The system was cooled to 5° C and stirred for another 30 minutes, after which is was suction-filtered. The crystals were rinsed with 25 ml of a 50% aqueous solution of ethyl alcohol and dried at room temperature and under reduced pressure in the presence of anhydrous calcium chloride for 5 hours. The procedure provided 4.1 g of β-crystals of d-α-isobutylsulfobenzylpenicillin.½ mol ethyl alcohol.

EXAMPLE 8

In 50 ml of ethanol was dissolved 5 g of d-α-isobutylsulfobenzylpenicillin.½ mol isopropyl alcohol crystals and, at 15° C, 50 ml of water was added dropwise over a period of 60 minutes, whereupon crystals formed. The system was cooled to 5° C and, following the addition of 150 ml of water, it was stirred at that temperature for 2 hours. It was then suction-filtered and the crystals were rinsed with 25 ml of a 20% aqueous solution of ethyl alcohol, followed by drying under reduced pressure and at room temperature in the presence of anhydrous calcium chloride for 5 hours. The procedure provides 4.0 g of α-crystals of d-α-isobutylsulfobenzylpenicillin.½ mol ethyl alcohol.

The following is a tabulation of the physical and chemcial data on the compounds of this invention as produced in the foregoing examples.

Table 1

| Physical and chemical constants Example No. | $[\alpha]_D^{20}$ $CHCl_3, c=1.0$ | Gas-chromatography weight % of solvent | Characteristic infrared absorptions (KBr, cm$^{-1}$) | NMR (60 MHz, ppm, $d_6$-DMSO) |
|---|---|---|---|---|
| 1 | +133° | Diisopropyl ether 9.6 % | 1550, 1670, 1765, 1790, | 1.05(d,6H), 3.45(m,H), 0.85(d,6H), 1.5(s,3H), 1.65(s,3H), 3.95(d,2H), 4.22(s,H), 5.55(d,2H), 5.78(s,H), 7.46(m,5H), 1.9(m,H) |
| 2 | +138° | Isopropyl alcohol 5.9 % | 1550, 1670, 1765, 1790 | 1.00(d,3H), 3.75(m,0.5H), 0.85(d,6H), 1.5(s,3H), 1.65(s,3H), 3.95(d,2H), 4.22(s,H), 5.55(d,2H), 5.78(s,H), 7.46(m,5H), 1.9(m,H) |
| 3 | +139° | Acetone 5.8 % | 1550, 1670, 1765, 1790 | 2.05(s,3H), 0.85(d,6H), 1.5(s,3H), 1.65(s,3H), 3.95(d,2H), 4.22(s,H), 5.55(d,2H), 5.78(s,H), 7.46(m,5H), 1.9(m,H) |
| 4 | +135° | Ethyl acetate 8.5 % | 1550, 1670, 1765, 1790 | 1.12(t,1.5H), 2.06(s,1.5H), 3.37(q,H) 0.85(d,6H), 1.5(s,3H), 1.65(s,3H), 3.95(d,2H), 4.22(s,H), 5.55(d,2H), 5.78(s,H), 7.46(m,5H), 1.9(m,H) |
| 5 | +141° | Ethyl alcohol (α-crystals) 4.7 % | 1550, 1670, 1765, 1790 | 3.45(q,H), 1.07(t,1.5H) 0.85(d,6H), 1.5(s,3H), 1.65(s,3H), 3.95(d,2H), 4.22(s,H), 5.55(d,2H), 5.78(s,H), 7.46(m,5H), 1.9(m,H) |
| 7 | +141° | Ethyl alcohol (β-crystals) 4.7 % | 1550, 1670, 1760, 1790 | 3.45(q,H), 1.07(t,1.5H) 0.85(d,6H), 1.5(s,3H), 1.65(s,3H), 3.95(d,2H), 4.22(s,H), 5.55(d,2H), 5.78(s,H), 7.46(m,5H), 1.9(m,H) |

The above crystals are invariably acicular (needles).

The above crystals are invariably acicular (needles).

EXPERIMENTAL

A shelf-life test was carried out at 40° C for each of the penicillin compounds indicated below. The results are also set forth below. The percent residue values were calculated from the spectral absorption data obtained by the Herriott method (Journal of Biological Chemistry, 64, 725 (1946)).

Table 2

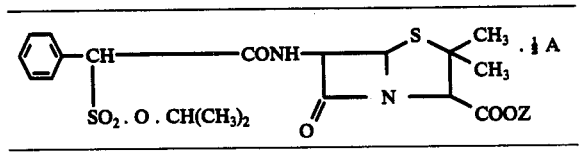

| Optical activity of α-position | Crystallinity | Z | A | Percent residue at 40° C 4 weeks | 9 weeks |
|---|---|---|---|---|---|
| Racemic | Amorphous | Na | None | 41 | 37 |
| Racemic | Amorphous | H | None | 48 | 41 |
| d | Amorphous | H | None | 76 | 57 |
| d | Crystalline (β-)** | H | Ethyl alcohol | 100 | 99 |
| d | Crystalline (α-) | H | Ethyl alcohol | 100 | 99 |
| d | Crystalline | H | n-Propyl alcohol | 100 | 98 |
| d | Crystalline | H | Acetone | 99 | 98 |
| d | Crystalline | H | Diisopropyl ether | 99 | 99 |
| d | Crystalline | H | Ethyl acetate | 98 | 98 |

Remarks**:
It appears that the great majority of β-crystals were transformed into α-crystals during storage at 40° C.

What is claimed is:

1. Pure d-α-Isobutylsulfobenzylpenicillin hemi-solvate crystals of the formula

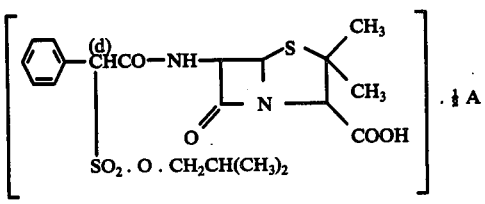

wherein A is a solvent selected from the group consisting of alcohols of 1 to 4 carbon atoms, ethers of 4 to 6 carbon atoms, ketones of 3 to 6 carbon atoms and esters of 3 to 6 carbon atoms.

2. Pure d-α-Isobutylsulfobenzylpenicillin hemi-solvate crystals as claimed in claim 1, wherein A is ethyl alcohol.

3. Pure d-α-Isobutylsulfobenzylpenicillin hemi-solvate crystals as claimed in claim 1, wherein A is diisopropyl ether.

4. Pure d-α-Isobutylsulfobenzylpenicillin hemi-solvate crystals as claimed in claim 1, wherein A is isopropyl alcohol.

5. Pure d-α-Isobutylsulfobenzylpenicillin hemi-solvate crystals as claimed in claim 1, wherein A is n-propyl alcohol.

6. Pure d-α-Isobutylsulfobenzylpenicillin hemi-solvate crystals as claimed in claim 1, wherein A is acetone.

7. Pure d-α-Isobutylsulfobenzylpenicillin hemi-solvate crystals as claimed in claim 1, wherein A is ethyl acetate.

* * * * *